(12) United States Patent
Philipp et al.

(10) Patent No.: US 12,196,937 B2
(45) Date of Patent: Jan. 14, 2025

(54) CONTEXT-DEPENDENT CONTROL OF A SURGICAL MICROSCOPE

(71) Applicant: Carl Zeiss Meditec AG, Jena (DE)

(72) Inventors: Markus Philipp, Aalen (DE); Stefan Saur, Aalen (DE); Christian Albrecht, Aalen (DE)

(73) Assignee: Carl Zeiss Meditec AG, Jena (DE)

( * ) Notice: Subject to any disclaimer, the term of this patent is extended or adjusted under 35 U.S.C. 154(b) by 570 days.

(21) Appl. No.: 17/455,274

(22) Filed: Nov. 17, 2021

(65) Prior Publication Data
US 2022/0163780 A1    May 26, 2022

(30) Foreign Application Priority Data
Nov. 20, 2020    (DE) ................. 10 2020 130 805.1

(51) Int. Cl.
*G02B 21/00*    (2006.01)
*G02B 21/36*    (2006.01)
*A61B 90/20*    (2016.01)

(52) U.S. Cl.
CPC ....... *G02B 21/0012* (2013.01); *G02B 21/365* (2013.01); *A61B 90/20* (2016.02)

(58) Field of Classification Search
CPC .. G02B 21/0012; G02B 21/365; G02B 21/00; G02B 21/0004; G02B 21/24; G02B 21/32; G02B 21/36; G02B 21/362; G02B 27/0093; G06N 20/00; A61B 90/20
USPC ............... 359/368, 362, 363, 369, 896, 900; 700/56, 57, 59, 60, 61, 62, 64, 65; 706/12, 15, 16, 25
See application file for complete search history.

(56) References Cited

U.S. PATENT DOCUMENTS

| | | | |
|---|---|---|---|
| 11,653,826 B2* | 5/2023 | Ushiroda | A61B 90/20 359/385 |
| 2009/0195688 A1* | 8/2009 | Henderson | G02B 21/245 348/E5.024 |
| 2018/0035054 A1* | 2/2018 | Sugie | H04N 23/683 |
| 2022/0104884 A1* | 4/2022 | Leiderman | A61B 1/000095 |

FOREIGN PATENT DOCUMENTS

| | | |
|---|---|---|
| DE | 10203215 A1 | 8/2003 |
| DE | 10 2014 113 935 A1 | 3/2016 |
| DE | 102018217903 A1 | 4/2020 |
| DE | 102019125418 B3 | 11/2020 |
| EP | 3593704 A1 | 1/2020 |

OTHER PUBLICATIONS

German Office Action, Application No. 10 2020 130 805.1, mailed Jun. 29, 2021, 13 pages.

* cited by examiner

*Primary Examiner* — Arnel C Lavarias
(74) *Attorney, Agent, or Firm* — Honigman LLP; Brett A. Krueger (57) ABSTRACT

A parameterization of a control algorithm of a surgical microscope is carried out on the basis of one or more context parameters of an operation. On the basis of the parameterization, the control algorithm then is applied to one or more state indicators associated with a first setting of the surgical microscope in order thus to obtain a second setting of the surgical microscope. By way of example, the parameterization can comprise one or more prioritization operations.

20 Claims, 7 Drawing Sheets

CONTEXT-DEPENDENT CONTROL OF A SURGICAL MICROSCOPE

CROSS-REFERENCE TO RELATED APPLICATIONS

This application claims priority of German Patent Application No. DE 10 2020 130 805.1 filed on Nov. 20, 2020, the contents of which are incorporated herein.

TECHNICAL FIELD

Various examples relate to the determination of settings for a surgical microscope. Various examples relate in particular to considering context parameters of the operation when determining settings.

BACKGROUND

The prior art has disclosed surgical microscopes that offer very different items of information to a user, generally the surgeon, in the eyepiece. By way of example, DE 10203215 A1 describes a surgical microscope that comprises a camera which generates an electronic image signal. The image signal is displayed on an electronic eyepiece which comprises a corresponding display apparatus for the electronic image data. Further items of information may also be output there. A surgical microscope is also known from DE 10 2014 113 935 A1.

Typical surgical microscopes have a multiplicity of possible settings. It can often require much outlay to choose a good setting during the operation.

EP3593704 is known, inter alia, and discloses an assisting endoscope which derives actions on the basis of image processing and a database of previous surgeries. A manually created database is used in this case. Such techniques often have restricted flexibility and are therefore sometimes inaccurate.

SUMMARY

Therefore there is a need for techniques which determine a setting for a surgical microscope.

This object is achieved by the features of the independent patent claims. The features of the dependent patent claims define embodiments.

A setting for a surgical microscope is determined automatically in the various examples. In this case, a target conflict between, on the one hand, a suitable setting and, on the other hand, an undisturbed workflow during the operation can be resolved by virtue of the expected optimal setting being determined independently and consequently the cognitive load being reduced.

Further, various examples describe how a further target conflict caused by different requirements of different assistance functionalities can be resolved during the automatic determination of the setting for the surgical microscope.

A method for controlling a surgical microscope during an operation on a patient comprises the determination of one or more state indicators. The one or more state indicators are associated with at least one first setting of the surgical microscope. The method also comprises the implementation of a parameterization of a control algorithm of the surgical microscope on the basis of one or more context parameters of the operation. Moreover, the method comprises the application of the control algorithm to the one or more state indicators in order to thus determine a second setting of the surgical microscope.

Thus, this means that a control algorithm can initially be suitably set by way of the parameterization and is subsequently used to determine the second setting of the surgical microscope.

In general, the second setting of the surgical microscope can differ from the at least one first setting.

By way of example, the second setting of the surgical microscope could be obtained by adapting one or more of the at least one first setting of the surgical microscope.

The one or more state indicators can be determined for example on the basis of a monitoring of the operation and/or on the basis of microscopy images of the surgical microscope.

In this case, the microscopy images can be captured using the at least one first setting of the surgical microscope.

As a result of parameterizing the control algorithm it is possible to determine the second setting in such a way that the latter is adapted to the best possible extent to a requirement of the surgeon, i.e., facilitates a best possible assistance of the surgeon during the operation.

The method can furthermore comprise triggering an application of the second setting. To this end it is possible, for example, to provide appropriate control data for the surgical microscope.

The control algorithm can be applied continuously, i.e., it is possible to continuously determine and apply new settings for the surgical microscope.

In this way there can be a continuous interaction between the surgeon and the control algorithm as the operation progresses because the control algorithm is newly parameterized to the context parameters altered by actions of the surgeon. Moreover, actions of the surgeon can have an effect on the state indicators.

There are different variants to carry out the parameterization. By way of example, the parameterization can comprise carrying out at least one prioritization operation. The prioritization operation can prioritize certain processes within the control algorithm over other processes. The prioritization operation can prioritize certain variables within the control algorithm over other variables.

By way of example, it would be possible to carry out a prioritization within candidate state indicators. These candidate state indicators can be determined using different metrics on the basis of the microscopy images of the surgical microscope. Thus, this means that different properties or features of the microscopy images can be considered in order to determine the various candidate state indicators. By way of example, different quality features could be taken into account. A semantic content of the microscopy images could be evaluated differently depending on the metric. By way of example, the different metrics could be associated with different assistance functionalities for the surgeon.

What can be achieved by the prioritization within the candidate state indicators is that different properties of the microscopy images are considered to a different extent, for example depending on the context of the operation. This is based on the discovery that different properties of the microscopy images may have a different importance to the surgeon depending on the context of the operation and during the course of the operation.

As an alternative or in addition thereto, it would be possible to carry out a prioritization within candidate control models of the control algorithm. These candidate control models can be used to ascertain settings of the surgical microscope on the basis of one or more state indicators. Thus, expressed differently, such candidate control models can translate state indicators into possible settings of the surgical microscope, from which the final second setting can then be selected.

Such techniques are based on the discovery that depending on the context of the operation different approaches for finding settings of the surgical microscope can be particularly expedient or can work particularly accurately.

As an alternative or in addition thereto, it would be possible for the prioritization to be carried out within candidate settings of the surgical microscope which are obtained by at least one control model of the candidate control models.

By way of example, if different variants for the setting of the surgical microscope are present it is possible to choose a particularly suitable setting, specifically on the basis of the context of the operation, for example.

The at least one prioritization operation can be carried out to resolve one or more target conflicts. Such a target conflict can be characterized by different settings of the surgical microscope, depending on the result of the prioritization operation.

Thus, a target conflict might be present if different settings of the surgical microscope are conceivable. Then, one of these different settings can be preferred as a result of the prioritization operation.

In this case, the prioritization operation can be applied near the final setting in the processing procedure, that is to say by prioritization within the candidate settings, or else be applied upstream within the processing procedure, for example by prioritization within the candidate control models or even further upstream by prioritization within candidate state indicators.

The at least one prioritization operation may comprise filtering and/or weighting the candidate state indicators and/or the candidate control models and/or the candidate settings.

By way of example, filtering may comprise discarding a candidate state indicator or a candidate control model or a candidate setting, with however a respectively different candidate being kept.

The weighting can keep a plurality of appropriate candidates but consider these to different extents in the subsequent processing procedure. In this way a flexible prioritization can attain particularly accurate results. It would be possible for the one or more context parameters to comprise one or more of the following elements: a surgical device, for example a surgical tool; a region of interest of the operation; a user stipulation; a phase of the operation; a type of operation; activities of the operation; planning data for the operation; and/or at least one surgeon involved in the operation. There can be a particularly comprehensive and flexible parameterization by way of such different elements which are taken into account in conjunction with the context.

The one or more context parameters can also comprise a prediction for a future progress of the operation.

As an alternative or in addition thereto it would be possible for the one or more context parameters to comprise a previous, preceding course of the operation.

The one or more context parameters can also describe a current actual state of the operation.

By way of example, the further course of the operation could also be predicted from a previous course of the operation and the current state of the operation.

By way of example, such a prediction could take account of the fact that the operation has already progressed during the time taken to determine and possibly apply the second setting. This delay can then be considered by the prediction of the course of the operation within the scope of the context parameter.

It would be possible for at least one context parameter of the one or more context parameters to be determined on the basis of a monitoring of the behaviour of the surgeon involved in the operation.

By way of example, to this end there could be an application of surround sensors, voice recognition could be used, the motion behaviour of the surgeon could be taken into account and/or the input of the surgeon via a human-machine-interface could be taken into account, to name but a few examples.

In particular, such techniques can facilitate an individual determination of the context depending on the surgeon, and hence can facilitate a targeted parameterization of the control algorithm.

The monitoring of the operation which is taken into account when determining one or more state parameters could for example relate to a number and/or an arrangement of one or more regions of interest of the operation in the patient. The regions of interest might be particularly indicative for the state of the operation. Specifically, the regions of interest can denote the regions focussed on by the surgeon. By way of example, a region of interest of the operation can refer to a region within the situs or the entire situs, which is of interest in an appropriate context of the operation.

This allows the state of the operation to be evaluated well in relation to the regions of interest. Accordingly, it would then be conceivable for an associated state parameter to evaluate, e.g., the visibility or recognizability of features within the region of interest in a microscopy image of the surgical microscope. As an alternative or in addition thereto the operation could be monitored on the basis of a specified model of the operation, which may comprise user-specific variants, for example. By way of example, this means that the specific course of the operation can be compared to a template provided by the model. By way of example, the regions of interest, for instance according to the phase of the operation, can be determined by the model. By way of example, it would be possible to monitor deviations between the specific operation and a template by the model and a region of interest or, more generally, a state indicator could be determined on the basis of such deviations. The parameterization itself could be carried out on the basis of an appropriate algorithm. A corresponding algorithm could be machine-learned. By way of example, reinforcement learning could be used. Such reinforcement learning can be trained on the basis of feedback which comprises a difference between the second setting of the surgical microscope determined by the control algorithm and a manually selected setting of the surgical microscope.

In this way, the parameterization could implement the stipulations of the corresponding surgeon with increasing accuracy as a result of a continuous interaction between the surgeon and the parameterization algorithm. A separate training phase can be dispensed with.

By way of example, the one or more state indicators could be determined on the basis of metrics which are applied to the microscopy images.

Different metrics are conceivable. By way of example, the metrics could evaluate one or more of the following properties of microscopy images: an image quality; a semantic content of the microscopy images; and/or a visibility of regions of interest in the microscopy images.

By way of example, the image quality could denote a brightness and/or a contrast and/or a colour space of the microscopy images. In this respect, the image quality can be independent of the semantic content of the microscopy images, i.e., for example, independent of the visibility of a certain region of interest.

By way of example, a check could be carried out as to whether reflections are present within a certain region of interest.

By way of example, a check could be carried out as to whether a particularly low contrast is present within a certain region of interest.

By way of example, a check could be carried out as to whether there is a saturation in a certain region of interest of the pixel values of the various pixels of the microscopy images which image the corresponding region of interest.

By way of example, different state indicators could be associated with different assistance functionalities. In turn, these assistance functionalities can be associated with different metrics.

The metrics may cause an above-described target conflict. This may be the result of the different metrics assessing the same properties of the microscopy images contrariwise.

The monitoring of the operation can relate to at least one of the following: a course of the operation; an actual state of the operation; and/or a progress of the operation in relation to a target state. By way of example, it would be conceivable for a specified model of the operation to be taken into account to this end. By way of example, the progress of the operation can describe a degree of fulfilment of one or more targets defined by the specified model.

By monitoring the operation on the basis of such criteria it is possible in particular to monitor a deviation from certain stipulations and one or more state indicators can be determined on the basis thereof. Then, these are particularly meaningful in order to bring about a corresponding adjustment of the setting of the surgical microscope which facilitates an attainment of the stipulations.

The control algorithm could comprise one or more control models. Such a control model is configured to determine a candidate setting of the surgical microscope on the basis of at least one corresponding state indicator.

By way of example, machine-learned algorithms can be used as control models. Machine-learned algorithms of the various control models can be trained separately.

By way of example, this can allow the provision of a modular control algorithm which can be flexibly extended. Certain control models can be interchanged. New control models can be added. Old control models can be removed.

A computer program or a computer program product or a computer-readable storage medium comprises program code. The latter can be loaded and executed by a processor. The processor executing the program code causes the processor to carry out a method for controlling a surgical microscope during an operation on a patient. The method comprises the determination of one or more state indicators. The one or more state indicators are associated with at least one first setting of the surgical microscope. The method also comprises the implementation of a parameterization of a control algorithm of the surgical microscope on the basis of one or more context parameters of the operation. Moreover, the method comprises the application of the control algorithm to the one or more state indicators in order to thus determine a second setting of the surgical microscope.

A device comprises a processor. The processor is configured to determine one or more state indicators on the basis of a monitoring of an operation and further on the basis of microscopy images of a surgical microscope which are captured using at least one first setting of the surgical microscope. The one or more state indicators are associated with the at least one first setting of the surgical microscope. Moreover, the processor is configured to carry out a parameterization of a control algorithm of the surgical microscope on the basis of one or more context parameters of the operation. Further, the processor is configured to apply the control algorithm to the one or more state indicators in order to thus determine a second setting of the surgical microscope. This use of the control algorithm is based on the parameterization.

The features set out above and features that are described below may be used not only in the corresponding combinations explicitly set out, but also in further combinations or in isolation, without departing from the scope of protection of the present disclosure.

DETAILED DESCRIPTION

The properties, features and advantages of this disclosure described above and the way in which they are achieved will become clearer and more clearly understood in association with the following description of the exemplary embodiments which are explained in greater detail in association with the drawings.

The present disclosure is explained in greater detail below on the basis of preferred embodiments with reference to the drawings. In the figures, identical reference signs denote identical or similar elements. The figures are schematic representations of various embodiments of the disclosure. Elements illustrated in the figures are not necessarily illustrated as true to scale. Rather, the various elements illustrated in the figures are rendered in such a way that their function and general purpose become comprehensible to the person skilled in the art. Connections and couplings between functional units and elements as illustrated in the figures can also be implemented as an indirect connection or coupling. A connection or coupling can be implemented in a wired or wireless manner. Functional units can be implemented as hardware, software or a combination of hardware and software.

Various examples of the disclosure relate to the determination of a setting of a surgical microscope during the operation. Different settings of the surgical microscope can be determined in the various examples described herein. By way of example, it would be conceivable for relative positioning, i.e., a distance and/or orientation (pose), of the surgical microscope to be determined in relation to the patient undergoing the operation. As an alternative or in addition thereto, it would also be possible to determine settings of the optical system in the surgical microscope, for example a magnification (zoom), an illumination intensity and/or a contrast. It would also be possible to determine a mode of operation, for example the use of indirect or direct illumination, or illumination with light at a certain wavelength. A fluorescence mode could be activated. Video settings could be used.

Various examples are based on the discovery that a manual determination and application of settings—for instance manual repositioning of the surgical microscope—may represent an additional cognitive and mental load for the executing surgeon during the operation. By way of example, manual repositioning requires a "free hand", and so the surgeon must put down the surgical instruments or await a pause for a change of the surgical instruments. If the surgical instruments are put down in a dedicated step manual repositioning leads to an interruption of the operation. If the surgeon waits for a suitable window of opportunity for the repositioning there is the risk of the surgeon at least in part carrying out the operation with sub-optimal settings for the surgical microscope. Accordingly, it is possible to automatically determine the settings of the surgical microscope in accordance with the various examples described herein.

Moreover, the settings of the surgical microscope can be applied automatically following the determination.

A reference implementation for automatic determination of the setting of the surgical microscope would be, e.g., tracking the head of the surgeon. Then, the surgical microscope can follow the head movements. Various examples are based on the discovery that such an automatic control method is faced with the following applicative problem in particular: During surgery, the physician sets the microscope such that the visualization meets their demands. The physician sets the microscope on the basis of their experience; in the process the physician subconsciously makes compromises, as should be elucidated using the example of the choice of zoom level: On the one hand, the microscope should be set so that the surgeon can clearly see details of a vessel, for example. This would require a high magnification of the vessel. On the other hand, the surgeon would like to be able to work "quickly" in the situs, wherein a zoom level that is too high would be disadvantageous. A further example consists of the surgeon liking to see the surgical instruments situated in the situs centrally in the image. Since the instruments are at different locations on the image and both instruments cannot be in the centre of the image at the same time, the surgeon must also find a compromise in this case. The surgeon solves this target conflict subconsciously.

According to various examples it is possible to automatically solve such a target conflict between different possible settings of the surgical microscope. In some examples, the subconscious setting of a compromise between various target conflicts, learned by the surgeon, can be implemented algorithmically.

Such techniques are based on the discovery that conventional manual setting of the surgical microscope often has a target conflict between optimal visualization and unimpeded workflow. Frequent repositioning is required to attain an average high visualization quality but frequent repositioning also increases the cognitive load or number of workflow interruptions.

In the various examples described herein, a context of the operation is considered in conjunction with the determination of settings of the surgical microscope. In this case, the context of the operation can be described by one or more context parameters. The context of the operation can describe a situation in which the operation is found. As a general rule, the context can comprise all objects, regions of interests, actors and actions in the operating theatre. By way of example, the context can be captured by motion sensors, image processing, speech processing, etc. The context or a corresponding context parameter can be determined by the analysis of the situs and use of the surgical microscope. The context can also comprise anticipated future actions. The current context can therefore be used to predict future objects, actors and actions during the operation. Example: The next operation phase can be predicted on the basis of video data and an operation phase model. Further example: The region of interest in which the surgeon wants to primarily work in future (derived, e.g., from the time spent).

Very different context parameters can be taken into account as a general rule. Some of these context parameters are listed below in Table 1.

TABLE 1

| | Brief description | Exemplary details |
|---|---|---|
| I | Surgical tool | By way of example, a context parameter could be used to indicate which surgical tool is currently being used. What surgical tool has already been used or will be used in future during the respective operation could also be indicated. By way of example, the context parameter could specify an ID number and/or a type number of the respective surgical tool. The utilized surgical instruments or surgical tool can be taken into account. |
| II | Region of interest in the patient | By way of example, it would be possible to specify which region of interest or regions of interest are relevant to the surgeon, either currently or in future during the operation. As a general rule a region of interest can describe, for example, an anatomical region or an anatomical feature in the patient which requires the attention of the surgeon in the context of the operation. By way of example, the region of interest could denote the region of the surgical intervention (situs), or a portion thereof. The context parameter could specify the region of interest in parameterized form, that is to say for example "2 cm around the tooltip". The context parameter could already annotate the region of interest in a microscopy image of the surgical microscope. |
| III | User stipulation | The user could manually determine one or more context parameters - for example pre-surgery. By way of example, this would allow user preferences to be represented. By way of example, historic user data and/or use data could be taken into account. It would also be conceivable for user feedback to be provided at the runtime. User inputs can be taken into account. The user stipulation could be stored in a user profile, for example. |
| IV | Phase of the operation | An operation can typically be subdivided into a plurality of sections or phases. The different phases of an operation may be associated with different regions of interest, for example. The different phases of an operation can also be associated with different medical devices |

TABLE 1-continued

| | Brief description | Exemplary details |
|---|---|---|
| | | or surgical instruments (tools). |
| V | Type of operation | By way of example, the type of operation can describe a basic form of the surgical intervention. By way of example, the following would be conceivable types of operation: spinal column; microbiological intervention; head; brain; eye; etc. |
| VI | Surgeon | A certain type of operation can follow different courses depending on the surgeon. By way of example, different surgeons have different preferences in relation to the region of interest in the patient which should be represented, for example, in microscopy images on the surgical microscope. Different surgeons may also implement different types of intervention. It would be possible in some examples to dynamically monitor the behaviour of the surgeon during the operation. In this way it may then be possible to react even to changes in the course of the operation which are dynamically prompted by the surgeon during surgery. |
| VI | Analysis of the situs | By way of example, it would be conceivable to determine one or more characteristics of the situs of the operation by means of an image analysis of image data captured pre-surgery and/or during surgery. By way of example, it would be possible to determine placement and/or extent. By way of example, imaging techniques such as magnetic resonance imaging or computed tomography could be used to this end. |
| VII | Activities during the operation | By way of example, it would be conceivable to monitor certain landmarks of the course of the operation. By way of example, it is possible to monitor certain milestones in a model of the operation being reached. This could correspond to a phase of the operation, cf. Example IV.VIII |
| VIII | Movement pattern of the surgical instruments | By way of example, movement patterns of the surgical instruments could be monitored, for example by object recognition in the corresponding image data or by way of active tracking. |
| IX | Randomization | Sometimes it is also possible to take account of a randomized component in conjunction with the context parameter. Randomization is traced back to the concept of an algorithm recognizing that it understands the context only insufficiently and then nevertheless is able to provide an acceptable (albeit non-optimal) decision basis for determining the setting by way of randomization. |
| X | Planning data for the operation | By way of example, planning data captured pre-surgery or specified planning data could be taken into account. These can, but need not be available as user stipulations. |

Table 1: Examples of different context parameters that can be taken into account in conjunction with the parameterization of the control algorithm. As a general rule, the context parameters can be defined in conjunction with an actual state of the operation, meaning for example that these describe a current phase of the operation or a current region of interest in the patient. However, as an alternative or in addition thereto it would also be conceivable for the one or more context parameters to comprise a prediction about the future progress of the operation. Thus, it would be conceivable for a context parameter to specify a future region of interest. This can facilitate an anticipatory adjustment of the setting of the surgical microscope.

Depending on the information content of the context parameters it is possible to use different techniques for determining the context parameters. Some context parameters can be specified statically, i.e., read from a memory. Other context parameters can be determined, e.g., dynamically, for instance during surgery. By way of example, different sensor data could be used to this end. It is possible to use a corresponding algorithm for determining the one or more context parameters, for example a machine-learned method.

According to various examples one or more context parameters—cf. Table 1—of the operation are used in conjunction with determining a setting of the surgical microscope. In this case, the one or more context parameters of the operation are used in conjunction with the parameterization of a control algorithm which is configured to determine the setting of the surgical microscope. In this case, parameterization means that one or more parameters of the control algorithm are set depending on the one or more context parameters, for example this means that corresponding processing boundary conditions are pre-set accordingly before, specifically, an output is calculated. A possible example of the parameterization would be the prioritization between different settings and/or results of the control algorithm. By way of example there could be a selection between a plurality of sub-algorithms. Inputs could be taken into account in filtered or weighted fashion. It would be possible for different calculations to be subsequently carried out, depending on the parameterization, when ascertaining an output on the basis of an input. Taking into account the one or more context parameters within the scope of the parameterization can in particular differ from taking into account one or more inputs when determining an output by the control algorithm. The inputs of the control algorithm correspond to variables which directly influence the result, i.e., the output, of the control algorithm. Then again, the parameterization corresponds to a basic configuration of the control algorithm.

The implementation of the parameterization can be carried out in turn by an algorithm (algorithm for the parameterization). The algorithm for the parameterization can receive one or more context parameters as an input and can carry out the parameterization of the control algorithm on the basis thereof. By way of example, the algorithm for the parameterization could use a machine-learned method. In particular, reinforcement learning could be used. In this case, a loss function could be defined on the basis of a difference between the setting for the surgical microscope as determined by the control algorithm and a setting of the surgical microscope following a manual readjustment by the surgeon. The algorithm for the parameterization can be trained on the basis of this loss function, wherein the control algorithm itself may remain fixed, however.

The control algorithm is applied to one or more state indicators in the various examples. This means that the one or more state indicators represent the input of the control algorithm.

In general, the state indicators could describe features of the operation. In this case, the state indicators can describe a state associated with at least one first setting of the surgical microscope, wherein the control algorithm then determines a second setting of the surgical microscope that differs from the at least one first setting. By way of example, the second setting can represent an adjustment of one or more of the at least one first setting. By way of example, the at least one first setting could currently be in use and/or comprise one or more settings used earlier.

As a general rule, the state indicators can characterize individual features of the visualization quality. Exemplary state indicators would be, e.g.: relative position of regions of interest in the field of view of the microscope (viewing angle of the cameras); concealment of regions of interest on surgical instruments or the situs by surgical instruments or tissue of the situs; and/or illumination of the situs by comparing the position of a region of interest with an optical axis.

In general terms it is possible for the one or more state indicators to be determined on the basis of microscopy images of the surgical microscope. Thus, it would be conceivable for the one or more state indicators to be determined on the basis of microscopy images from the surgical microscope, using one or more specified metrics.

The one or more specified metrics can thus map the microscopy images on the set of state indicators. As a general rule, very different properties of the microscopy images can be taken into account in this case when determining the state indicators. By way of example, it would be conceivable that an image quality of the microscopy images is evaluated. To a first approximation, the image quality can be evaluated independently of the semantic content of the microscopy images in this case, for example independently of the represented anatomical features or other objects imaged of the microscopy images. By way of example, the image quality could relate to a brightness and/or a contrast of the microscopy images. However, as an alternative or in addition thereto it would also be possible for at least one of the one or more metrics to also evaluate a semantic content of the images. By way of example, the visibility of certain anatomical features or, phrased more generally, of regions of interest in the patient could be evaluated. By way of example, the visibility could be impaired by concealment, for instance by surgical instruments, or by reflections.

In this case the state indicators can quantitatively describe such features, as described above. It would be conceivable for the state indicators to each be associated with a corresponding target stipulation, and to each describe the degree of fulfilment of this target stipulation. By way of example, a state indicator could count the number of reflections and there could be a threshold for the number of reflections as a target stipulation.

Depending on the form of the metric it is possible to use very different techniques for the algorithmic implementation of a corresponding algorithm for determining the state indicators. By way of example, if the semantic content of microscopy images is evaluated, an object recognition could be used to determine the state indicators. If the image quality, for example the brightness or the contrast, is assessed it would be possible to carry out a histogram analysis of brightness values of the microscopy images. A corresponding (sub-)algorithm can be part of the control algorithm.

By way of example, it would be conceivable that the various state indicators are associated with different assistance functionalities for the surgeon. It is then possible for state indicators to be obtained by different metrics which are applied to the microscopy images of the surgical microscope, wherein the different metrics are associated with the different assistance functionalities. Examples of assistance functionalities would be, e.g.: homogeneous illumination of the situs; visibility of a certain region of interest; suppression of reflections on the image; etc.

By virtue of using different metrics it is possible to assess the same properties of the microscopy images differently. This is due to the fact that the visibility of a certain region of interest may be important for a first assistance functionality for example, with the visibility of this same defined region of interest possibly being unimportant to a second assistance functionality. Thus, this means that the different metrics (for instance of the various assistance functionalities) assess the same properties of the microscopy images contrariwise. Accordingly there is a target conflict which can be expressed by the corresponding state indicators associated with the various assistance functionalities.

In general, target conflict can mean that a plurality of target stipulations—e.g., in conjunction with different assistance functionalities or more generally different metrics for evaluating microscopy images in the form of the state indicators—should be simultaneously fulfilled to the best possible extent. In this context, target conflict means that the target stipulations are contrary to one another—for example comprehensive overview when working (low magnification of the situs) versus a detailed representation of the vessels in the situs (high magnification). Since the surgical microscope only has one parameter for the zoom setting the latter cannot simultaneously fulfil both target stipulations.

As a general rule it would be possible in this case for the state indicators to be determined dynamically. This means that the state indicators are determined intermittently—e.g., also in real time, i.e., with a cycle frequency of e.g. 20 Hz or faster. Thus, it is possible for the state operators to also be determined on the basis of a monitoring of the operation. In particular, it would be conceivable that an associated target stipulation also depends on the monitoring of the operation. This means that it is possible to determine whether the microscopy images captured by a current or a preceding setting of the surgical microscope are appropriate in conjunction with, for instance, a current state or course of the operation. This means that different state indicators can be obtained, optionally dynamically on the basis of the course of the operation, and so in each case different results for the setting of the surgical microscope are obtained dynamically. In this way, it is possible to react to the respective situation of the operation and a respective setting can be selected.

The monitoring of the operation can denote, e.g., a course of the operations, an actual state of the operation and/or a progress of the operation in relation to a target state. The monitoring of the operation could also relate to a prediction for a future state of the operation.

In this case, the monitoring of the operation can relate to, e.g., a number and/or arrangement of one or more regions of interest of the operation within the patient. As a general rule, a region of interest can be the general designation for a region in the situs which is of interest to the surgeon. By way of example, regions of interest can include anatomical features (tumour, nerves, . . . ), events in the situs such as haemorrhaging, navigation data, planned trajectories, fibre tracts, . . . . However, regions of interest can also be "attached" to the tip of a surgical instrument and then moved with the surgical instrument.

Then, it is possible—depending on the state of the operation—for different regions of interest to be relevant to the surgeon. It would be possible for the monitoring of the operation to be based on a specified model of the operation. The model of the operation can specify one or more intended courses of the operation. The regions of interest can also be defined in conjunction with such intended courses. It is conceivable for such a model to comprise user-specific variants. As a general rule, different courses may be stored in a model for the operation.

Figure 1:
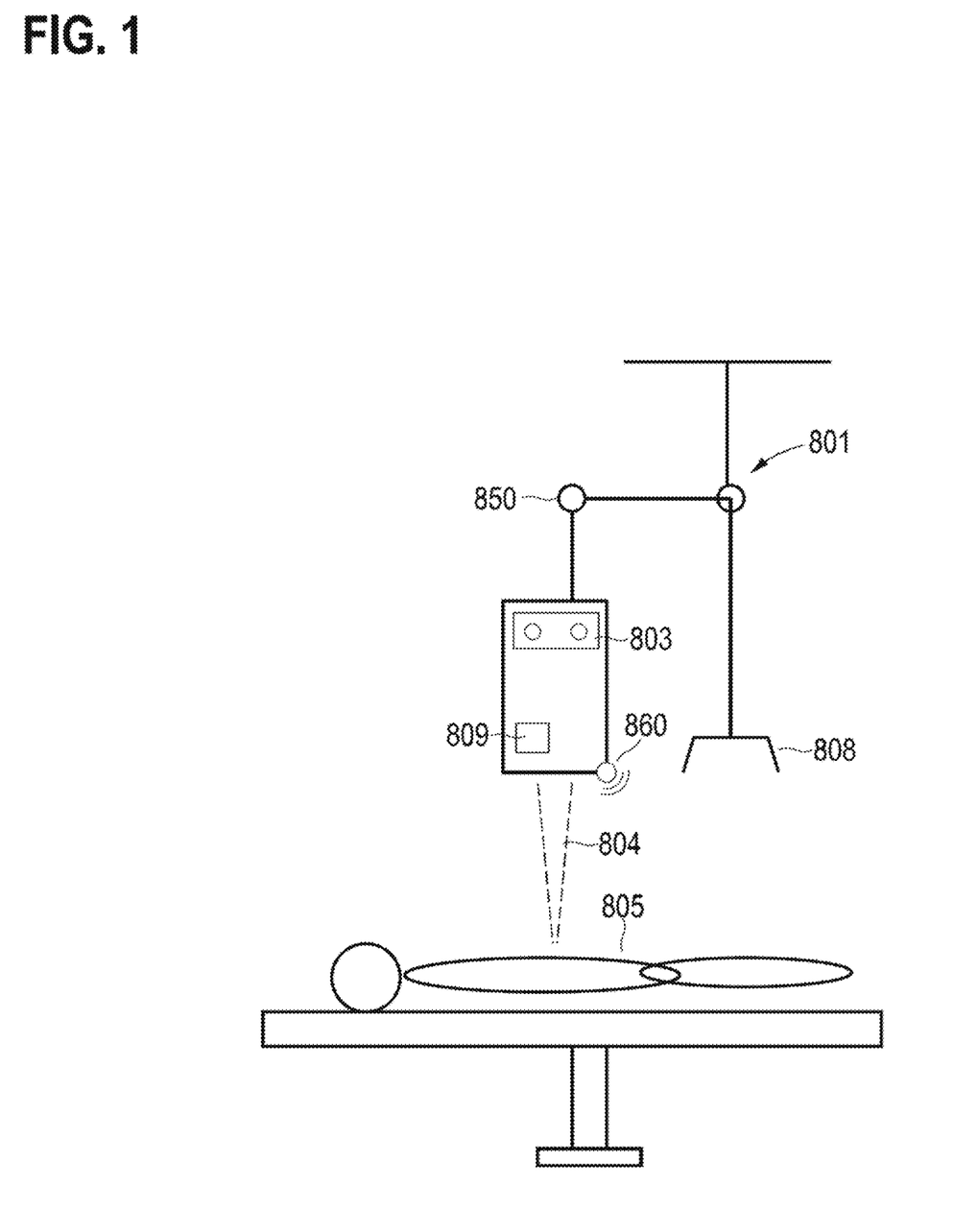
FIG. 1 schematically illustrates a surgical microscope as per various examples.

FIG. 1 schematically shows a surgical microscope 801 for surgery. In the illustrated example, the surgical microscope 801 comprises an eyepiece 803. Through the eyepiece 803, the surgeon can observe magnified images of an object which is situated in a field of view 804 of the surgical microscope 801. In the illustrated example, this is a patient 805 lying on a patient couch.

As an alternative or in addition to an optical eyepiece, provision could also be made for a camera which transmits images to a screen (digital surgical microscope).

An operating device 808 is also provided as a human-machine interface; by way of example, it can be embodied as a handle or a foot switch. It is a handle in the illustrated embodiment of FIG. 1. The operating device 808 allows the eyepiece 803, which is fastened to crossbeams 850, to be moved. Motors can be provided in order to automatically carry out the movement on the basis of control data, in accordance with a corresponding setting of the surgical microscope. The motors could also assist the movement prompted by the handle 808.

Further, a control device 809 is provided for the surgical microscope 801 and controls the operation of the combination microscope and the display of images and additional information and data in the eyepiece 803. The control device 809 can interact with the surgeon. By way of example, the control device 809 could alter a setting of the surgical microscope on the basis of appropriate control data. To this end, one or more actuators could be controlled, for instance to move the crossbeam, to change an optical unit, etc. The setting can also comprise the digital post-processing of sensor data. The setting could also relate to data capture parameters, for instance for captured digital images. It would also be possible to switch between different image sources or imaging modes, depending on the setting.

The surgical microscope 801 can also comprise one or more further sensors 860, for instance a motion sensor or a thermal imaging camera or a microphone or a surround camera, etc. Such further sensors 860 can also be operated differently depending on the setting of the surgical microscope.

In neurosurgery, surgical microscopes are used to visualize low-lying structures in narrow cavities. Depending on the type of operation it is necessary for the surgical microscope to adopt a new viewing direction relative to the situs approximately every minute since a new concealment situation arises, by way of example, on account of altered positions of the instruments. In surgical microscopes that are currently commercially available it is necessary to this end for the surgeon to reposition the system manually, i.e., they clasp, e.g., a handle attached to the microscope side and guide the system into a new pose (position & orientation of the microscope).

Figure 2:
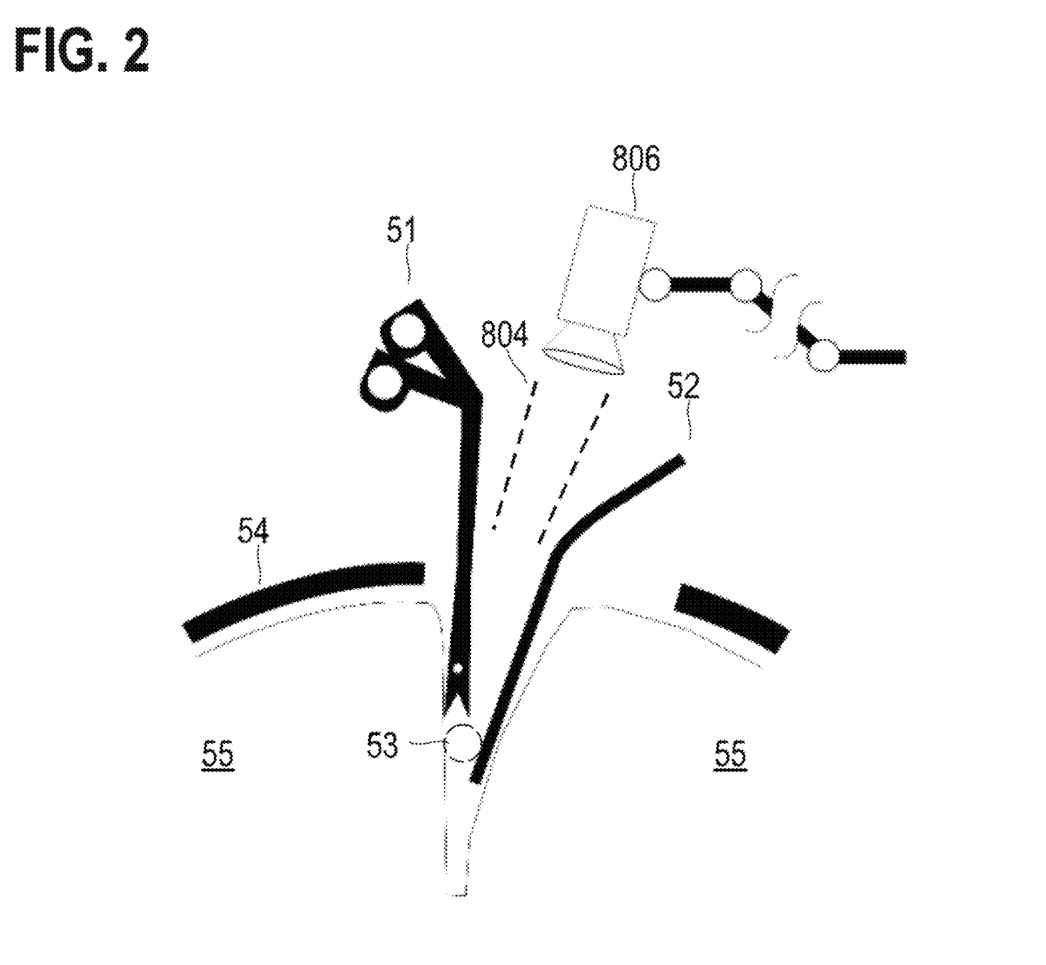
FIG. 2 schematically illustrates a region of interest of an operation and the relative positioning of the surgical microscope in relation to the region of interest according to various examples.

FIG. 2 illustrates an exemplary positioning of an optical unit 806 of the surgical microscope 801 in relation to a situs 53 within the skullcap 54 of a patient 55. Moreover, surgical instruments 51, 52 are illustrated. In the various examples described herein it is possible for the relative positioning of the surgical microscope 801 for instance of the light microscope 806, in particular in relation to the patient to be determined within the scope of setting the surgical microscope 801 and this can optionally also be adapted automatically, for example by virtue of a corresponding stand comprising mechanical actuators. The relative positioning can comprise a distance and/or orientation (pose).

Figure 3:
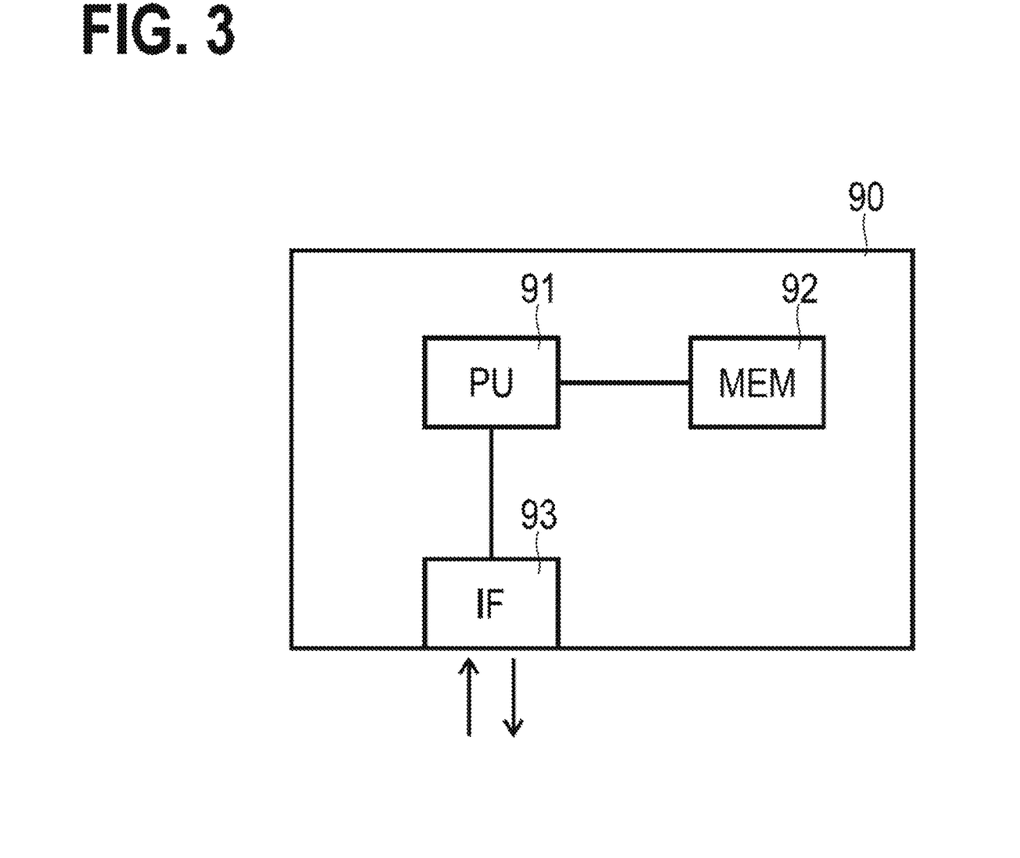
FIG. 3 schematically illustrates a device for data processing in accordance with various examples.

FIG. 3 schematically illustrates a device 90 that can be used for the data processing in the various examples described herein. By way of example, the device 90 could be a PC or a cloud server. The device 90 comprises a processor unit 91, a non-volatile memory 92, and an interface (IF) 93. The processor unit 91 can load program code from the non-volatile memory 92 and execute said code. This causes the processor unit 91 to carry out techniques according to the examples described herein, for example parameterizing a control algorithm which is configured to determine a setting of the surgical microscope for example a second setting proceeding from one or more first settings; determining one or more state indicators associated with a current setting of the surgical microscope, for example on the basis of microscopy images from the surgical microscope and optionally using a suitable metric; etc.

Figure 4:
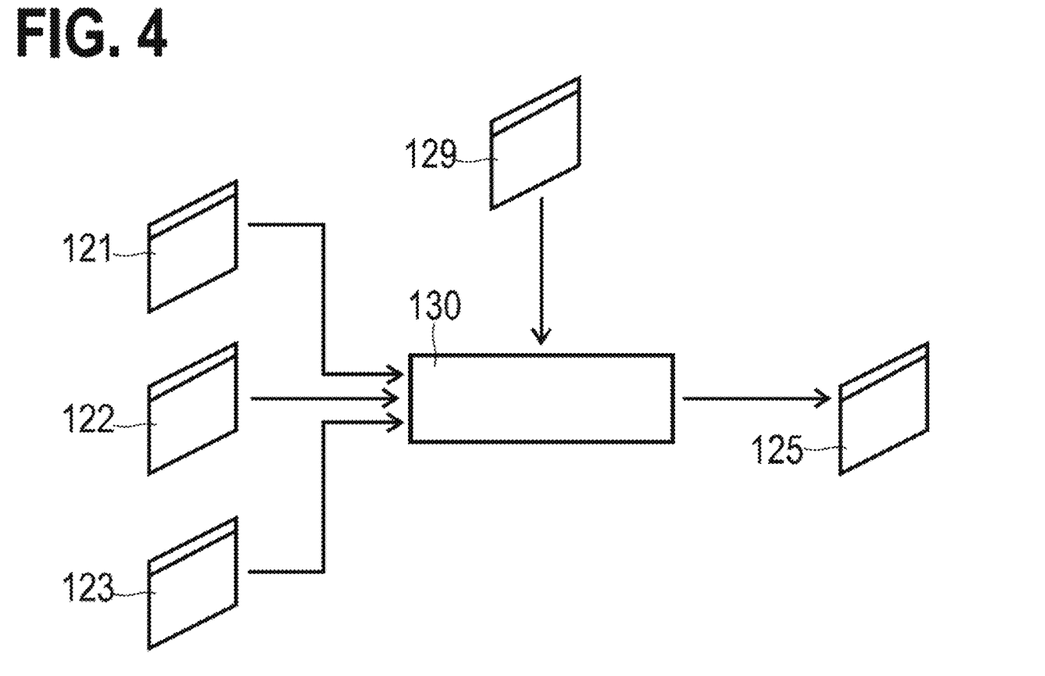
FIG. 4 schematically illustrates a control algorithm as per various examples.

FIG. 4 illustrates aspects in connection with the control algorithm 130. As an output the control algorithm 130 provides a setting 125 of the surgical microscope. By way of example, the setting could be described by way of appropriate control data which are subsequently transmitted to the control device 809. The setting of the surgical microscope 801 could be implemented automatically on the basis of the control data.

This setting 125 can also be referred to as second setting if it is determined proceeding from at least one first setting.

As an input, the control algorithm 130 in the example of FIG. 4 receives a plurality of state indicators 121-123 which are associated with the at least one first setting of the surgical microscope 801, that is to say, for example, with the current setting of the surgical microscope or else, for example, with one or more earlier settings. As a general rule, the control algorithm 130 could also receive only a single state indicator or two or more state indicators as an input. The control algorithm 130 could even determine the state indicators 121-123 itself in some examples.

The state indicators 121-123 can be determined on the basis of microscopy images of the surgical microscope (captured with a respective first setting) and/or further on the basis of a monitoring of the operation, that is to say, for example, on the basis of corresponding state data. By way of example, different state indicators 121-123 can be associated with different metrics which are applied to the microscopy images. The different metrics can be associated with different assistance functionalities, for example. The different state indicators 121-123 can describe how well the respectively associated first setting fulfils a certain target stipulation described by the respective metric. By way of example, a certain assistance functionality may demand visibility of a certain region of interest; if the corresponding region of interest is not visible or only visible to a restricted extent in the microscopy images, the respective state indicator can indicate a poor correspondence with this stipulation.

FIG. 4 further illustrates that the control algorithm 130 is parameterized on the basis of a context parameter 129. This means that one or more parameters of the control algorithm 130 are adapted depending on the value of the context parameter 129. By way of example, a prioritization could take place. In turn, the context parameters could be associated with the at least one first setting of the surgical microscope. This means that the context parameter 129 can describe the context of the operation in the case of the respectively activated first setting.

As a general rule, more than a single context parameter 129 could also be used for the parameterization. Examples of context parameters were described above in conjunction with Table 1.

What can be achieved by virtue of the control algorithm 130 being parameterized on the basis of the context parameter 129 is that the setting 125 can be determined particularly reliably and dynamically. In this way it is possible, in particular, to resolve target conflicts which might result from state indicators 121-123 associated with different metrics and possibly different assistance functionalities. Phrased more generally, it is possible to resolve target conflicts that might result from different stipulations in relation to the setting 125.

Figure 5:
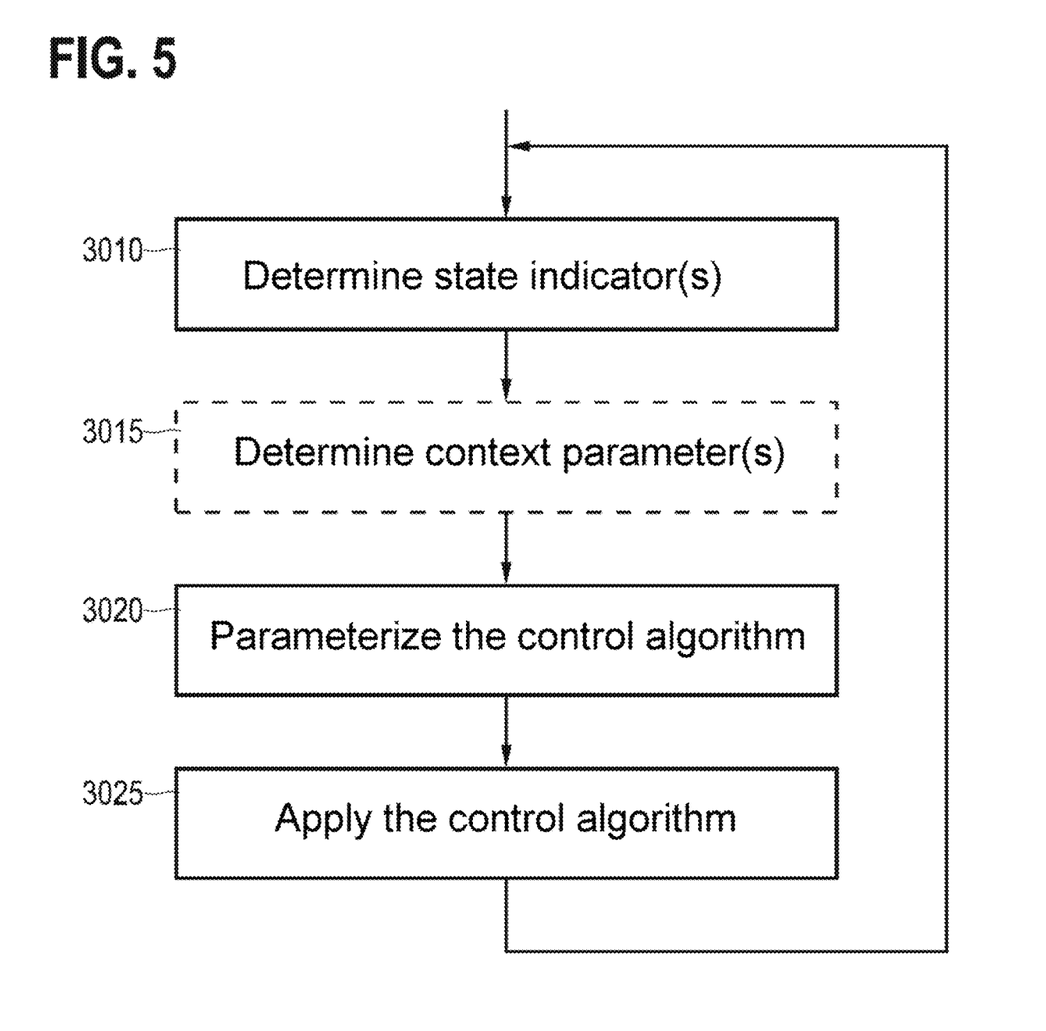
FIG. 5 is a flowchart of one exemplary method.

FIG. 5 is a flowchart of an exemplary method. By way of example, the method of FIG. 5 could be carried out by the device 90, for example by the processor unit 91, on the basis of program code that is loaded from the memory 92. Optional boxes are illustrated using dashed lines.

Initially one or more state indicators are determined in Box 3010. This is based on the operation being monitored—i.e., for example, on the basis of one or more state data—and further on microscopy images of the surgical microscope. By way of example, use could be made of one or more metrics which—depending on the state of the operation—assess the microscopy images, for example in respect of fulfilling one or more stipulations.

By way of example, the operation could be monitored in respect of one or more regions of interest. It would be possible to carry out a continuous identification of regions of interest. Firstly, a region of interest can be determined by sensor signals, such as tool movements, for example. Secondly, there is the option of extracting regions of interest by way of image processing approaches. Thus, tool positions/movements, haemorrhaging, blood vessels, nerves or tumour regions, for example, can be extracted from image data. It would also be possible to define regions of interest as regions with increased activity, for example by way of tool tips. Moreover, there is the option of extracting regions of interest by including a surgical navigation system. By way of example, the planned trajectory and the current trajectory to the region of interest can originate from a navigation system.

In this case, the one or more state indicators can be associated with at least one first setting of the surgical microscope.

One or more context parameters are optionally determined in Box 3015. If the context parameters are not determined dynamically it would be possible for these to be predefined pre-surgery.

Examples of context parameters were elucidated above in conjunction with Table 1.

Then, the control algorithm is parameterized in Box 3020. This is implemented on the basis of the one or more context parameters in Box 3015.

As a general rule, a further algorithm (algorithm for the parameterization) could be used for the parameterization. By way of example, the latter could be machine-learned. By way of example, use could be made of an artificial neural network. The machine-learned algorithm could be trained in a training phase. The training phase could be separate from the actual inference phase, which occurs during the operation. However, the use of reinforcement learning would also be conceivable. In this case, a comparison could be made as to whether the second setting of the surgical microscope ascertained by the control algorithm is changed to a manually selected setting of the surgical microscope or whether it is adopted by the surgeon. A loss function for the training can be defined on the basis of a deviation between the manually selected setting and the setting determined by the control algorithm.

Then, the control algorithm can be applied in Box 3025 in order to obtain the second setting of the surgical microscope.

It would be possible for this second setting of the surgical microscope to then also be applied, for example by virtue of appropriate control data being transmitted to the control device of the surgical microscope. This corresponds to an action to change setting parameters of the surgical microscope.

The actions of Box 3010-3025 can optionally be repeated multiple times in order thus to determine dynamic settings for the surgical microscope. This could be implemented in real time, for example, that is to say with a cycle frequency that is no slower than, e.g., 25 Hz, for example.

Next, examples of the parameterization of the control algorithms 130 in Box 3020 are described. In particular, the parameterization can comprise the prioritization of parameters of the control algorithm 130. This is explained in detail below.

In this case, the prioritization can be implemented in different ways within the sequence of logical operations of the control algorithm 130, specifically by the prioritization of the available state indicators, control models for ascertaining settings of the surgical microscope and/or between different candidate settings.

Phrased in general, the prioritization can thus mean that certain state indicators, control models and/or settings are selected or weighted on the basis of one or more context parameters.

The parameterization of the control algorithm can thus comprise the implementation of at least one prioritization operation. A few examples for these prioritization operations are described below in Table 2.

TABLE 2

| | Examples of prioritization operations | Exemplary description |
|---|---|---|
| I | Prioritization within candidate state indicators | By way of example, if a plurality of candidate state indicators are present (cf., e.g., FIG. 4 where a plurality of candidate state indicators 121-123 are present) then one or more state indicators can be selected from this set and can be processed further in the control algorithm. This means that an input layer of the control algorithm can carry out filtering in the context of the candidate state indicators. Non-utilized candidate state indicators can then be discarded. As an example, a concealment of a region of interest, for example, could be problematic in a certain context of the operation (e.g., if the bipolar coagulator optically conceals the area to be coagulated) while concealment may be unproblematic in a different context (e.g., if the aspirator conceals the bipolar only briefly). If it is recognized on the basis of a context parameter that concealment critically reduces the visualization quality then a state indicator which quantifies the "concealment" is prioritized and used to determine the setting. By way of example, this is implemented by virtue of, e.g., a pose which reduces the concealment that is problematic for the visualization quality being ascertained when determining the setting. Thus, this means that the activation of the corresponding setting of the surgical microscope improves the corresponding state indicator which quantifies the "concealment" (i.e., brings it better into correspondence with a corresponding target stipulation). Other state indicators might not be taken into account or only taken into account to a subordinate extent. On the basis of the current course of the operation and a corresponding context parameter, a current region of interest is determined as being located away from the centre of the field of view of the surgical microscope and hence there no longer is optimal illumination of the region of interest. Since this |

TABLE 2-continued

| Examples of prioritization operations | | Exemplary description |
|---|---|---|
| | | region of interest has already been detected for a specified time period the anticipated future action is that the surgeon wishes to continue to work in this region of interest. A state indicator which quantifies the currently incorrect illumination is therefore prioritized and in this way an adjusted illumination is determined as an action as a setting of the surgical microscope. Other state indicators might not be taken into account or only taken into account to a subordinate extent. |
| II | Prioritization within candidate control models | By way of example, the control algorithm can comprise different candidate control models which can be used to ascertain settings of the surgical microscope on the basis of at least one state indicator and optionally an associated target stipulation. By way of example, different candidate control models can comprise different approaches for generating appropriate control data. Different degrees of freedom of the surgical microscope can be addressed. It would be possible to then select one or more of these candidate control models. |
| III | Prioritization within candidate settings | It would be conceivable that a plurality of candidate settings - of one or more candidate control models - are received. It is then possible to select the setting output at the end (also referred to as "second setting" above) from the corresponding set. Thus, it is possible for the control algorithm to carry out appropriate filtering between the candidate settings. |

Table 2:Examples of prioritization operations. It is possible for the prioritization to comprise a combination of such prioritization operations and/or further prioritization operations. The prioritization operation can be carried out to resolve at least one target conflict. The target conflict can be characterized by different settings of the surgical microscope, depending on the result of the prioritization operation. This means that—depending on the result of the prioritization—a setting is obtained for the surgical microscope 801 in each case and different results of the prioritization are associated with different settings. These can be formed contrariwise, i.e., a target conflict is present. Thus, this means that the prioritization operation resolves the target conflict to the benefit of the ultimately determined setting. This is achieved by virtue of the candidate state indicators and/or candidate control models and/or candidate settings being taken into account in weighted fashion and/or being filtered (i.e., some elements are discarded).

The various examples of prioritization operations as per Table 2 are described in more detail below in conjunction with FIG. 6, FIG. 7, FIG. 8 and FIG. 9.

Figure 6:
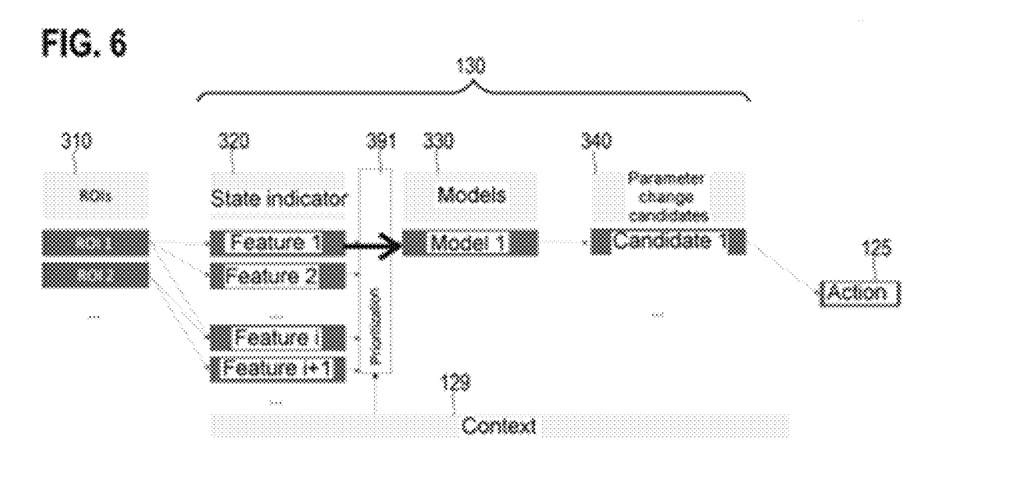
FIG. 6 schematically illustrates a parameterization of a control algorithm as per various examples.

FIG. 6 illustrates aspects in connection with the control algorithm 130. As an input, the control algorithm 130 receives a plurality of candidate state indicators 320 (these can correspond to the state indicators 121-123 as per FIG. 4).

The candidate state indicators 320 are determined in advance on the basis of a monitoring of the operation and microscopy images. In the illustrated example, a plurality of regions of interest 310, in particular, are determined for the current state of the operation and the candidate state indicators 320 are ascertained on the basis thereof. To this end, a machine-learned method could be used, for example. By way of example, the candidate state indicators 320 may specify the quality of the visibility of the corresponding regions of interest 310 (denoted by "ROI" in the figures) in the microscopy images. However, as a general rule, other candidate state indicators 320 may also be determined, for example independently of the regions of interest 310.

Then, there is a prioritization operation 391 as per Table 2: Example I. This is because one of the candidate state indicators 320 is prioritized (thick arrow in FIG. 6, "Feature 1"), i.e., filtering is carried out in the illustrated case. This prioritization operation is carried out on the basis of one or more context parameters 129.

The corresponding state indicator 320 is then transmitted as an input to a control model 330, which ascertains a candidate setting 340 for the surgical microscope. This candidate setting 340 is then transmitted to the surgical microscope as a final setting 125 (also referred to as "second setting").

Figure 7:
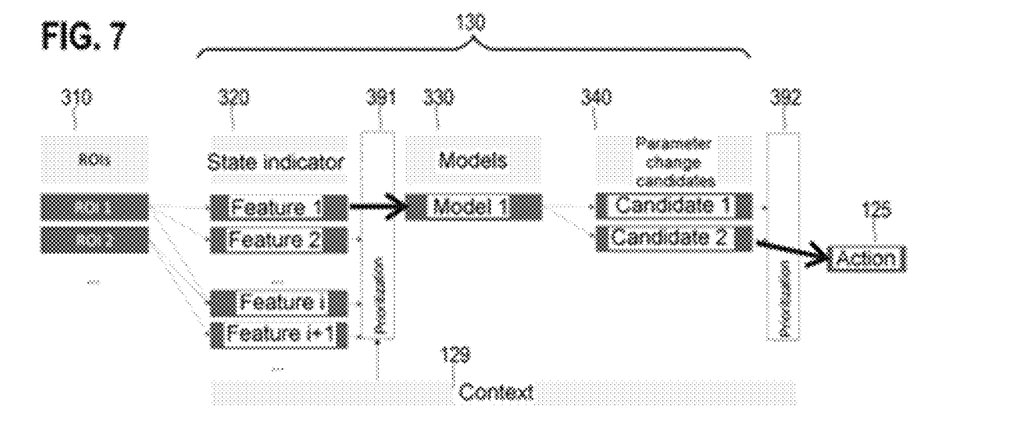
FIG. 7 schematically illustrates a parameterization of a control algorithm as per various examples.

FIG. 7 illustrates aspects in relation to the control algorithm 130. The example in FIG. 7 corresponds, in principle, to the example in FIG. 6. In the example of FIG. 7, the control model 330 however determines two candidate settings 340. Then, a prioritization is carried out among these candidate settings 340 within the scope of a further prioritization operation 392 in order to determine the setting 125, cf. Table 2: Example III.

Figure 8:
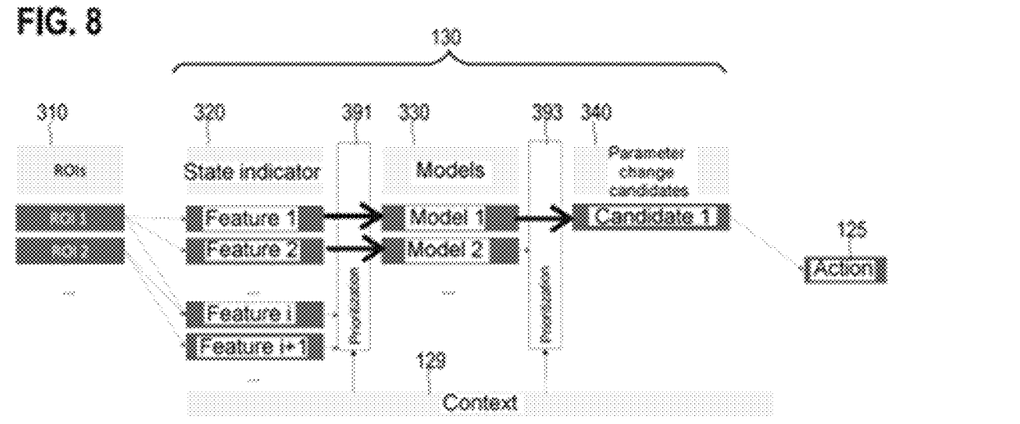
FIG. 8 schematically illustrates a parameterization of a control algorithm as per various examples.

FIG. 8 illustrates aspects in relation to the control algorithm 130. The example in FIG. 8 corresponds, in principle, to the example in FIG. 6. However, a plurality of candidate control models 330 are available in the example of FIG. 8. One of the candidate control models 330 is prioritized within the scope of a further prioritization operation 393 ("Model 1"; thick arrow) and used to determine the setting for the surgical microscope, cf. Table 2: Example II.

FIG. 8 illustrates that the various candidate control models 330 are associated with different state indicators. This may be the case because the candidate control models are associated with different assistance functionalities.

Figure 9:
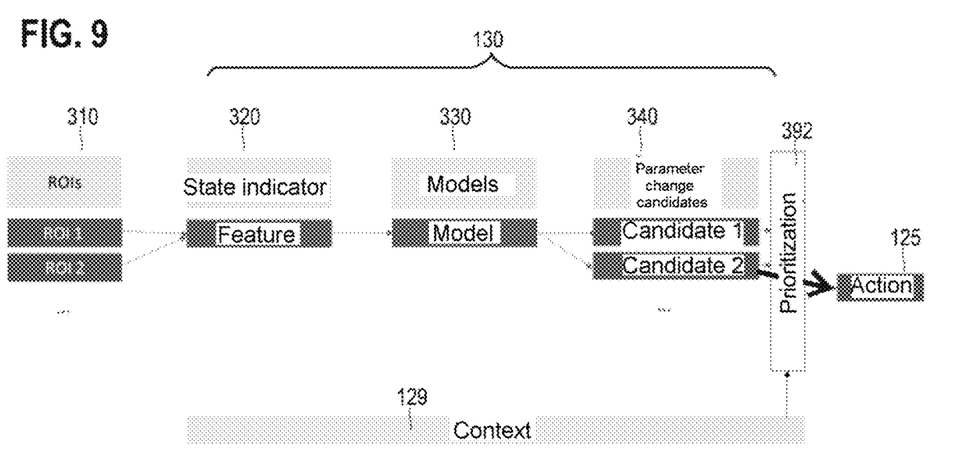
FIG. 9 schematically illustrates a parameterization of a control algorithm as per various examples.

FIG. 9 illustrates aspects in relation to the control algorithm 130. In this case, only the prioritization operation 392 is used.

As a general rule, it is possible to flexibly combine the various prioritization operations 391-393 with one another, or else use these on an individual basis.

Figure 10:
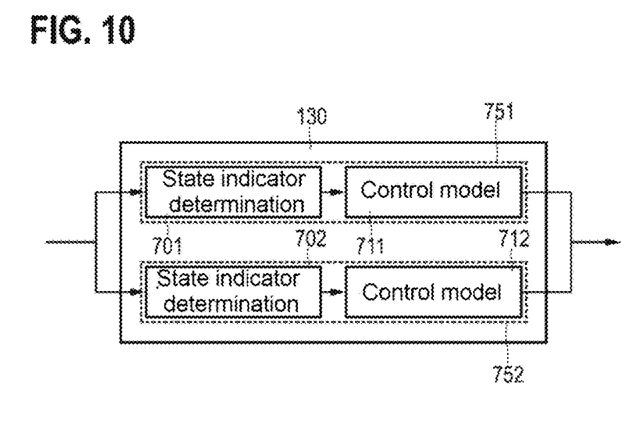
FIG. 10 illustrates an algorithmic implementation of a control algorithm as per various examples.

FIG. 10 illustrates aspects in connection with the control algorithm 130. In particular, FIG. 10 illustrates aspects in conjunction with the algorithmic implementation of the control algorithm 130.

The control algorithm 130 comprises a plurality of sub-algorithms 701-702, 711-712 in the example of FIG. 10. In this case, the sub-algorithms 701, 711 are associated with a first assistance functionality and the sub-algorithms 702, 712 are associated with a second assistance functionality.

The sub-algorithm 701 and the sub-algorithm 702 are configured to determine state indicators. To this end, the sub-algorithms 701-702 can each resort to a monitoring of the operation, for example for current regions of interest, and receive microscopy images of the surgical microscope as an input. By way of example, the sub-algorithms 701-702 can be machine-learned.

In this case it is possible in other examples for the determination of the state indicators to occur in advance of the control algorithm 130.

The sub-algorithms 701-702 then determine the state indicators and, on the basis of the state indicators, the control models 711-712 can each determine candidate settings. Target conflicts may arise in the process.

As a general rule, the control algorithm 130 could be implemented in monolithic or modular fashion.

In the case of a monolithic implementation, various sub-algorithms 701-702, 711-712 of the control algorithm 130 are implemented together and trained together in the case of machine-learned sub-algorithms. By way of example, the sub-algorithms 701-702 which are configured to determine the state indicators 320 can be implemented together. The control models 711-712 can also be implemented together.

In the case of a modular implementation different sub-algorithms 701-702, 711-712 of the control algorithm 130 can be implemented in at least partly separated fashion. In the case of machine-learned sub-algorithms these can be trained separately. By way of example, different sub-algorithms can be associated with different assistance functionalities (assistance functionalities 751, 752 are illustrated in the example of FIG. 10). By way of example, different sub-algorithms 701-702 which are configured to determine the state indicators 320 could be used; these can be trained separately. Such an implementation is advantageous in that in the case of changes in one or more sub-algorithms these can be replaced on an individual basis without influencing the training for other sub-algorithms.

An example for an application of the control algorithm 130 which is associated with the two assistance functionalities 751-752 is described below:

The assistance functionality 751 is configured to obtain an optimal homogeneous illumination of the situs in the microscopy images from the surgical microscope. Hence, the region of interest is the entire situs. On the basis of the microscopy images captured repeatedly during the surgery, a mean brightness and a uniform distribution of the brightness in the image are determined as state indicators, in each case by the sub-algorithm 701. By way of example, this could be implemented by a histogram analysis. Then, on the basis of specified mapping of brightness to luminous intensity of the surgical microscope, the control model 711 determines the required luminous intensity of the surgical microscope 801 as a candidate for the setting.

The assistance functionality 752 is configured to avoid reflections in the tissue around the tool tip. In this case, the region of interest is a region defined 2 cm around the tool tip. In this case, the corresponding tools, i.e., surgical instruments, can be identified in image-based fashion by the application of machine learning, for instance by the sub-algorithm 702. Then, the number of reflections in the region of interest is determined by the sub-algorithm 702 as a state indicator. To this end, the sub-algorithm could carry out a histogram analysis and/or machine learning. The control model 752 can then determine the required luminous intensity as a candidate for the setting—on the basis of specified mapping between the number of reflections and the luminous intensity of the surgical microscope 801. A target conflict may arise from the two candidates for the setting: The assistance functionality 751 states "brighter" for better light while the assistance functionality 752 states "darker" for fewer reflections.

Then it would be possible to prioritize between the two candidate settings on the basis of a context parameter; cf. Table 2, Example III. In this example, the context parameter could describe an operation phase; cf. Table 1, Example IV.

A first operation phase could relate to working toward the aneurysm: in this case, the surgeon would for example prefer a good illumination even in the peripheral regions of the situs (maintaining overview) and, in return, accept reflections in their specific working region. A second operation phase relates to aneurysm clipping: in this case, the surgeon would prefer, for example, to have fewer interfering reflections in the image and, in return, accept a slightly worse peripheral illumination.

In the case of the modular solution the assistance functionalities 751, 752 of the example above could be developed and tested independently since the context knowledge and the learned prioritization is only included between the steps of "models" and "parameter change candidates". The context extraction could also be learned independently of the assistance functionalities.

Changes to the assistance functionalities 751, 752 might also be undertaken since the prioritization already occurs at an earlier step in the pipeline. Nevertheless, essential components of the respective assistance functionality 751, 752 can continue to be adopted in this case.

A further example for the aforementioned techniques is described below.

A setting of the surgical microscope 801 (also referred to as "second setting" above) is determined on the basis of a control algorithm 130. Here, the control algorithm 130 comprises a control model (cf. FIG. 10, control models 711, 712) which is designed as a machine-learned algorithm, for example as an artificial neural network. The control model was trained in a training phase, for example on the basis of the following state indicators: (i) relative position of the region of interest in the field of view of the microscope (viewing angle of the cameras); concealment of regions of interest by surgical instruments or tissue in the situs. The corresponding adjusted setting of the surgical microscope 801 can be specified as "ground truth".

In this case, graduated values for the state indicators (e.g., how prominent the concealment is) can be determined continuously while the microscope is in use (e.g., on the basis of image processing).

Furthermore, it is however also conceivable to use state indicators which indicate—for instance on the basis of a course of the operation—a prediction in conjunction with a corresponding feature for a future point in time (e.g., a shortly anticipated degree of concealment). By way of example, this can be solved by neural networks which were trained in advance using real data.

During runtime, there is a situation-dependent prioritization of the state indicators in real time (cf. Table 2, Example I): It is possible to assume that surgeons reposition the microscope for one or more reasons. A reason for repositioning the microscope can consist of the view being impaired too much as a result of concealment. Or because an optimal illumination is no longer ensured. However, at the same time the surgeon also attempts to optimize other targets, e.g., distribution of the regions of interest in the image plane. Similar to the behaviour of the real surgeon, an attempt is made by way of the prioritization to prioritize those one or more state indicators which are indicative for a visual restriction.

To carry out this prioritization operation, the control algorithm includes the current, the past and the anticipated future context. This means that one or more context parameters are taken into account. To this end, use is made of machine learning-based methods which were trained on real data, for example.

It is conceivable for context parameters which describe a past state of the operation to be processed, e.g. by intelligent filters which distinguish between relevant events and irrelevant events. Furthermore, it is conceivable that neural networks with inputs (i.e., current and past context signals) make long-term or short-term context predictions which are included in the prioritization.

Thus, in summary, techniques were described above which describe a parameterization—for example a prioritization—of a control algorithm for a surgical microscope depending on a context of the operation. By way of example, a prioritization algorithm can be used to this end, the latter implementing one or more prioritization operations on the basis of one or more context parameters. Then, the surgical microscope can be controlled on the basis of a corresponding setting which is obtained from the control algorithm. By way of example, corresponding algorithms, i.e., the control algorithm and/or the prioritization algorithm, could be implemented on a suitable data processing unit.

In this case, the parameterization can be implemented in real time. One or more context parameters can be determined in real time, for example by means of an appropriate, possibly machine-learned algorithm. One or more state indicators can be determined in real time, for example by a machine-learned algorithm (cf. FIG. 10, sub-algorithms 701, 702, or else in advance of the control algorithm).

The operation can be monitored in real time. By way of example, one or more regions of interest for the operation could be determined in real time. A machine-learned method can be used to monitor the operation. By way of example, a machine-learned method could be used to determine regions of interest. A model for the operation can be taken into account. Monitoring the operation, for example in particular determining regions of interest, can be implemented continuously.

One or more control models which are suitable for determining a setting for the surgical microscope can be carried out in real time (cf. FIG. 10, sub-algorithms 711, 712). To this end, machine-learned methods can be used.

Rules-based methods can also be used as an alternative or in addition to machine-learned methods. Other examples relate to self-learning or learning methods, or behaviour-based methods.

It goes without saying that the features of the embodiments and aspects of the disclosure described above can be combined with one another. In particular, the features can be used not only in the combinations described but also in other combinations or on their own without departing from the scope of the disclosure.

By way of example, techniques were described above, in which a setting for a surgical microscope is determined on the basis of one or more state indicators. In this case, variants would be conceivable in which a setting is also ascertained for different surgical devices using corresponding techniques, i.e., a parameterization of the control algorithm on the basis of one or more context parameters.

The invention claimed is:

1. A method for controlling a surgical microscope during an operation on a patient, the method comprising:
on a basis of a monitoring of the operation and further on a basis of microscopy images from the surgical microscope captured with at least one first setting of the surgical microscope, determining one or more state indicators which are associated with the at least one first setting of the surgical microscope;
carrying out a parameterization of a control algorithm of the surgical microscope on a of one or more context parameters of the operation; and
on a basis of the parameterization, applying the control algorithm to the one or more state indicators in order to thus determine a second setting of the surgical microscope.

2. The method of claim 1, wherein the parameterization of the control algorithm comprises carrying out at least one prioritization operation selected from:
a prioritization within candidate state indicators, which are determined using different metrics on the basis of the microscopy images from the surgical microscope;
a prioritization within candidate control models which are used by the control algorithm to ascertain settings of the surgical microscope on the basis of the one or more state indicators; or
a prioritization within candidate settings of the surgical microscope which are obtained by at least one control model of the candidate control models.

3. The method of claim 2, wherein:
the at least one prioritization operation is carried out to resolve at least one target conflict; and
the at least one target conflict is characterized by different settings of the surgical microscope depending on a result of prioritization operation.

4. The method of claim 1, wherein the one or more context parameters of the operation comprise one or more of: a surgical device; a surgical tool; a region of interest of the operation; a user stipulation; a phase of the operation; a type of operation; activities of the operation; planning data for the operation; or at least one surgeon involved in the operation.

5. The method of claim 1, wherein the one or more context parameters comprise a prediction for a future progress of the operation.

6. The method of claim 1, further comprising:
determining at least one context parameter of the one or more context parameters on a basis of a monitoring of a behaviour of a surgeon involved in the operation.

7. The method of claim 1, wherein the monitoring of the operation relates to a number or arrangement of one or more regions of interest of the operation within the patient.

8. The method of claim 1, wherein the monitoring of the operation is implemented on a basis of a specified model of the operation, which optionally comprises user-specific variants.

9. The method of claim 1, wherein the parameterization is carried out on a basis of a machine-learned algorithm which is optionally trained by reinforcement learning on a basis of feedback, which comprises a difference between the second setting of the surgical microscope determined by the control algorithm and a manually selected setting of the surgical microscope.

10. The method of claim 1, wherein:
the one or more state indicators are determined on a basis of one or more metrics which are applied to the microscopy images; and
the one or more metrics evaluate one or more of the following properties of the microscopy images: an image quality; a semantic content of the microscopy images; or a visibility of regions of interest in the microscopy images.

11. The method of claim 10, wherein the one or more state indicators comprise a plurality of state indicators which are associated with different assistance functionalities and which are determined on a basis of different metrics.

12. The method of claim 11, wherein the different metrics assess the same properties of the microscopy images contrariwise.

13. The method of claim 1, wherein the monitoring of the operation relates to at least one of: a course of the operation; an actual state of the operation; or a progress of the operation in relation to a target state.

14. The method of claim 1, wherein:
the control algorithm comprises a plurality of control models, each of which is configured to determine a candidate setting of the surgical microscope on a basis of at least one corresponding state indicator of the one or more state indicators;

the plurality of control models each comprise a machine-learned algorithm; and the machine-learned algorithms of the plurality of control models are trained separately.

15. A device comprising a processor configured to carry out operations comprising:

on a basis of a monitoring of an operation and further on a basis of microscopy images from a surgical microscope captured with at least one first setting of the surgical microscope, determining one or more state indicators which are associated with the at least one first setting of the surgical microscope;

carrying out a parameterization of a control algorithm of the surgical microscope on a basis of one or more context parameters of the operation; and on a basis of the parameterization, applying the control algorithm to the one or more state indicators in order to thus determine a second setting of the surgical microscope.

16. The device of claim 15, wherein the parameterization of the control algorithm comprises carrying out at least one prioritization operation selected from:

a prioritization within candidate state indicators, which are determined using different metrics on the basis of the microscopy images from of the surgical microscope;

a prioritization within candidate control models which are used by the control algorithm to ascertain settings of the surgical microscope on a basis of the one or more state indicators; or a prioritization within candidate settings of the surgical microscope which are obtained by at least one control model of the candidate control models.

17. The device of claim 16, wherein;

the at least one prioritization operation is carried out to resolve at least one target conflict; and the at least one target conflict is characterized by different settings of the surgical microscope depending on a result of the prioritization operation.

18. The device of claim 15, wherein the one or more context parameters comprise one or more of: a surgical device; a surgical tool; a region of interest of the operation; a user stipulation; a phase of the operation; a type of operation; activities of the operation; planning data for the operation; or at least one surgeon involved in the operation.

19. The device of claim 15, wherein the one or more context parameters comprise a prediction for a future progress of the operation.

20. The device of claim 15, wherein the operations furthermore comprise:

determining at least one context parameter of the one or more context parameters on a basis of a monitoring of a behaviour of a surgeon involved in the operation.

* * * * *